(12) United States Patent
Wariar

(10) Patent No.: US 7,606,617 B2
(45) Date of Patent: Oct. 20, 2009

(54) URINALYSIS FOR THE EARLY DETECTION OF AND RECOVERY FROM WORSENING HEART FAILURE

(75) Inventor: Ramesh Wariar, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 619 days.

(21) Appl. No.: 11/343,441

(22) Filed: Jan. 31, 2006

(65) Prior Publication Data

US 2007/0179389 A1    Aug. 2, 2007

(51) Int. Cl.
*A61N 1/00* (2006.01)
(52) U.S. Cl. ...................................... 607/17
(58) Field of Classification Search ............. 607/17–18, 607/60; 600/300, 301, 481, 529–538, 500–508; 436/155; 705/4
See application file for complete search history.

(56) References Cited

U.S. PATENT DOCUMENTS

| | | | |
|---|---|---|---|
| 4,255,438 A * | 3/1981 | Kane et al. .................. 514/404 |
| 5,105,824 A | 4/1992 | Rasch | |
| 5,277,188 A * | 1/1994 | Selker ........................ 600/508 |
| 5,516,700 A | 5/1996 | Smith et al. | |
| 5,518,003 A | 5/1996 | Allan | |
| 5,558,638 A | 9/1996 | Evers et al. | |
| 5,730,149 A | 3/1998 | Nakayama et al. | |
| 6,290,646 B1 * | 9/2001 | Cosentino et al. ........... 600/300 |
| 6,312,378 B1 * | 11/2001 | Bardy ........................ 600/300 |
| 2001/0047000 A1 * | 11/2001 | Wolff et al. ............. 514/252.12 |
| 2003/0008860 A1 * | 1/2003 | Bakker-Arkema et al. .. 514/215 |
| 2003/0167862 A1 | 9/2003 | Hodges | |
| 2003/0190259 A1 | 10/2003 | Alley | |
| 2006/0051873 A1 * | 3/2006 | FitzGerald .................... 436/86 |
| 2006/0073606 A1 * | 4/2006 | Fukuda ........................ 436/155 |
| 2006/0224421 A1 * | 10/2006 | St. Ores et al. .................. 705/4 |
| 2006/0264376 A1 * | 11/2006 | Mitrovic et al. ................ 514/12 |
| 2007/0087387 A1 * | 4/2007 | Devarajan ................... 435/7.1 |
| 2007/0293740 A1 * | 12/2007 | Bardy ........................ 600/301 |

OTHER PUBLICATIONS

Casual Urine Concentrations of Sodium, Potassium, and Creatine in Polulation Studies of Blood Pressure, Abstract, Department of Public Health and Primary Care, Royal Free Hospital School of Medicine, London UK, Journal Human Hypertension, Dec. 4, 1990.*
*Cardiovascular Disorders—Nurse's Clinical Library*, Springhouse Corporation, Springhouse, PA, (1984), p. 83.

* cited by examiner

*Primary Examiner*—George Manuel
*Assistant Examiner*—Robert N Wieland
(74) *Attorney, Agent, or Firm*—Schwegman, Lundberg & Woessner, P.A.

(57) ABSTRACT

A system and method of detecting decompensation of heart failure for a patient includes urinalysis to determine the change in physical and/or chemical composition of a patient's urine over time. The change in chemical and/or physical composition of the patient's urine is used to infer the onset of decompensation. Optionally, the inference is verified with other data, such as with baseline transthoracic impedance data, patient weight data, and/or blood composition data.

32 Claims, 7 Drawing Sheets

URINALYSIS FOR THE EARLY DETECTION OF AND RECOVERY FROM WORSENING HEART FAILURE

TECHNICAL FIELD

This document generally relates to a system for performance of urinalysis, and more particularly to a system for performance of urinalysis to generate an early detection of impending decompensation of heart failure.

BACKGROUND

Heart failure is a condition wherein the heart fails to circulate blood sufficiently to meet the metabolic demands of the various tissues of the body. In advanced heart failure patients, cardiac output is maintained both by compensatory physiological mechanisms (such as salt and water retention, vasoconstriction, increased sympathetic activation, and cell growth), and therapy. This condition is referred to as compensated heart failure. These individuals may take various medications for their condition, may be on special diets, and may have cardiac rhythm management devices implanted within them to provide electrical therapies for their hearts (e.g., to synchronize cardiac contractions, and correct for unusually fast or slow beats). Despite these measures, patients usually undergo acute worsening of their heart failure condition during which the cardiac compensatory mechanisms are maladaptive and the patient suffers from hemodynamic abnormalities, respiratory distress, end organ failure, arrhythmias, and progressive heart failure. This condition is called acute heart failure decompensation. If the patient is not stabilized quickly, acute heart failure decompensation can be fatal. By managing their conditions carefully, patients may reduce the number of episodes in which they experience heart failure decompensation.

Multiple factors may precipitate heart failure decompensation. Some patients may deviate from their heart failure management regimen. Other times, decompensation occurs because of factors beyond the control of the patient such as pulmonary infection/embolism, atrial fibrillation, anemia, and renal insufficiency. In either event, early detection of impending decompensation of heart failure is important. If impending decompensation of heart failure is detected with sufficient warning, health care personnel may be able to examine the patient's condition prior to the event, and may be able to initiate therapies that ameliorate the patients condition. Despite the fact that multiple factors may precipitate decompensation, the predominant pathophysiological pathway leading to acute HF decompensation is salt and water retention that ultimately leads to fluid volume overload and pulmonary edema. Thus, if fluid volume overload can be detected early, health care personnel may recognize the patient's situation, and may respond, for example, by prescribing diuretics that remove fluid by increasing urine discharge. Existing methods for the detection of worsening heart failure measure events that may occur later in the cascade of fluid retention.

To allow for the possibility of delivering appropriate medical attention to a patient before the patient exhibits heart failure decompensation, it is desirable to obtain early warning. Preferably, the method by which warning is obtained is reasonably reliable, in order to reduce the number of "false alarms," so that medical attention can be visited upon those who need it, without also visiting such attention upon a great number of patients who are not in need of immediate medical attention.

SUMMARY

The foregoing reveals the desirability of a system and method for early detection of heart failure decompensation. According to one embodiment, a system for early detection of heart failure decompensation includes a first interface configured to receive urinalysis data, and to send the urinalysis data to a computer via a network. The system also includes a second interface configured to receive data from a cardiac rhythm management device, and to send the data from the device to the computer. Additionally the system includes a set of instructions stored in the computer, which when executed causes the computer to access the urinalysis data and the data from the cardiac rhythm management device, and based at least in part upon the accessed data, to detect decompensation of heart failure.

According to another embodiment, a method of early detection of decompensation of heart failure in a patient includes comparing a urinalysis measurement with a first boundary to determine if the urinalysis measurement is abnormal for the patient. The method also includes comparing a measurement made by a cardiac rhythm management device with a second boundary to determine if the device measurement is abnormal for the patient. Finally, the method includes determining whether decompensation of heart failure is imminent for the patient on the basis of the comparisons.

According to yet another embodiment, a computerized method of early detection of impending decompensation in a patient includes accessing a set of urinalysis data. Each datum within the data set describes a particular characteristic of the patient's urine at differing points in time. The method also includes determining a boundary from the accessed urinalysis data set. A data point describing the particular characteristic of the patient's urine is compared with the boundary. Impending decompensation of heart failure is detected for the patient, based at least in part upon the comparison.

According to yet another embodiment, a computerized method of early detection of decompensation of heart failure in a patient includes accessing a plurality of sets of urinalysis data. For a given one of the urinalysis data sets, each datum therein describes a particular characteristic of the patient's urine at differing points in time. Further, each of the urinalysis data sets corresponds to a different characteristic of the patient's urine. A plurality of boundaries is determined. Each of the boundaries corresponds to a given one of the plurality of urinalysis data sets. Each of a plurality of data points describing characteristics of the patient's urine is compared with a corresponding one of the plurality of boundaries. Impending decompensation of heart failure is detected for the patient, based at least in part upon the comparisons.

According to yet another embodiment, a system for early detection of decompensation of heart failure includes a means for obtaining urinalysis data and a means for detecting impending decompensation of heart failure, based upon the urinalysis data.

According to yet another embodiment during the recovery of the patient from heart failure decompensation the treatment may be adjusted based on remote monitoring of urinalysis data using the advanced patient management system.

DETAILED DESCRIPTION

Figure 1:
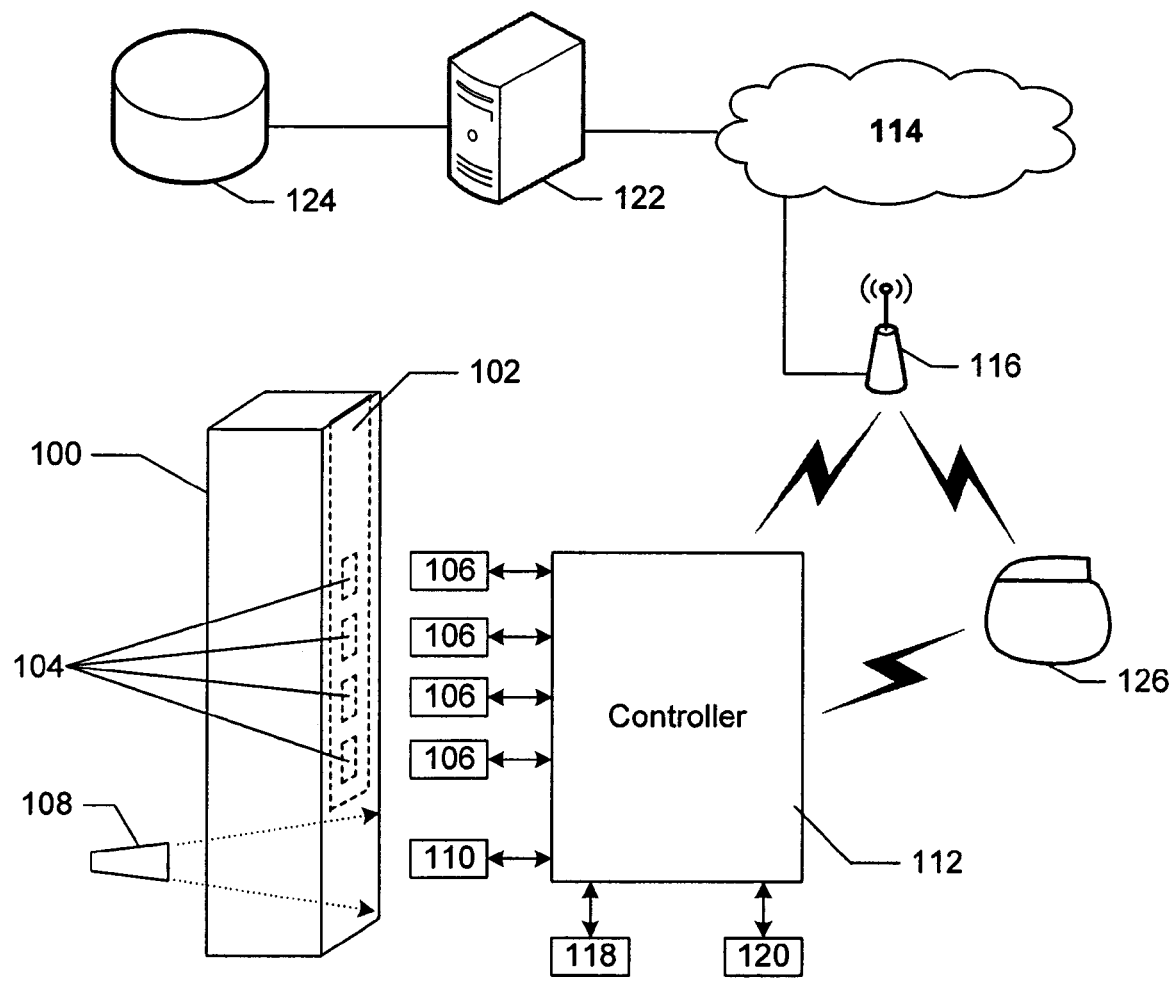
FIG. 1 depicts an exemplary embodiment of a system for the early detection of decompensation of heart failure.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

A variety of variables may be examined to detect the onset of decompensation of heart failure in a given patient. For example, as heart failure worsens, fluid is generally retained by the patient. Therefore, heart failure may be detected by observing the weight of a patient on a periodic basis (e.g., daily basis), and identifying sudden gains in weight, which may correspond to fluid retention.

Additionally, the fluid retained may cause the expansion of thoracic fluid volume and result in pulmonary edema which generally corresponds with a decrease in the baseline impedance exhibited across the thorax. Thus, heart failure may be detected by observing the transthoracic baseline impedance exhibited by a patient on a periodic basis (e.g., daily basis), and identifying sudden losses in impedance. Such impedance measurements may be made, for example, by cardiac rhythm management devices, such as pacemakers, cardiac resynchronization therapy (CRT) devices, cardiodefibrillators, and the like.

The foregoing indicators provide opportunities for improvement upon early detection of decompensation of heart failure. Given that fluid retention accounts for the majority of decompensation episodes, the measurement of body weight changes is the most common method in use for detecting worsening heart failure. An substantial increase in weight may signal that water is being retained. However this measurement is error prone because although fluid retention is associated with weight gain, the reverse is not necessarily true. A given patient may exhibit a gain in weight for reasons unrelated to fluid retention, meaning that early detection of worsening heart failure due to weight may be difficult due to nonspecific nature of the measurement.

With regard to transthoracic impedance, it is believed that this particular indicator may provide an earlier warning than observation of patient weight. For example, it is believed that during worsening heart failure, thoracic fluid increases only after the retention of sodium and water by the kidneys (Francis G S et al., Pathophysiology of Heart Failure, Hurst's The Heart, 11$^{th}$ Edition, McGraw-Hill, 2004, page 713, FIG. 24-8). Thus sodium and water retention if detected may be an earlier marker of fluid retention than thoracic fluid. Further thoracic fluid measurements may be difficult to obtain, and may be subject to error. For example, to the extent that the impedance measurements are obtained by an external device, the measurement may be sensitive to location of the leads. If the leads of the external device are not placed in precisely the same location on the patient's body with each successive measurement, the resulting impedance values may vary, even though the fluid content of the patient remains unchanged. On the other hand, if the measurements are taken by an implanted device, such as by a pacemaker or CRT device, then the measurements may be influenced by cyclical (e.g., respiration, cardiac cycle, etc.) and/or non-cyclical (e.g., posture) body effects.

To advance the art of detecting decompensated heart failure, urinalysis may be performed. Generally, as a patient begins to experience worsening heart failure, the kidneys retain fluid. Accordingly, the patient's urine contains relatively less fluid increasing the concentration of substances excreted. As this occurs, several effects are generally observed. The color of the urine tends to darken, for example. Also, the urine tends to be relatively denser, and therefore exhibits a greater specific gravity. Further, the concentration of certain urine constituents tends to either escalate or drop. For example, as heart failure worsens, the ratio of urine sodium to urine creatinine tends to drop.

Given the foregoing, it follows that a system may perform urinalysis to detect impending decompensated heart failure. The detection may be based upon many variables, including patient weight, transthoracic impedance (or bioimpedance measurements, such as an impedance measurement taken across a portion of a patient's leg—another anatomical site known to retain fluid during heart failure), and physical and chemical properties of the patient's urine. By blending the aforementioned variables, a system achieving early and reliable detection of decompensated heart failure is realized. Further, such a system may generally track renal function, for example, by measuring the capacity of the kidneys to clear various constituents from the blood plasma.

FIG. 1 depicts an exemplary embodiment of a system for early detection of decompensated heart failure and for tracking of renal function. The system includes a collection volume 100 for containing a urine sample. The collection volume 100 includes a chemically treated strip 102, which, in turn, includes one or more chemically treated pads 104. According to one embodiment, the strip 100 is disposed on the inside of the collection volume 100, so that each of the pads 104 is immersed in urine, when the volume is full. Each pad 104 changes state in proportion to the concentration of a given chemical constituent in the urine within the volume. For example, each pad 104 may change color in response to the presence of a different chemical constituent. Per such a scheme, the concentration of a given chemical constituent may be determined by observation of the color (e.g., color shade and/or intensity) of a corresponding pad 104. For example, a first pad 104 may change color based upon the concentration of protein within the urine sample, while a second pad may change color based upon the concentration of sodium within the sample. Other examples of constituents which may be tested for with the pads 104 include, without limitation, total protein, microalbumin, uric acid, urea, creatinine, leukocyte estrase, nitrites, bilirubin, ketones, and/or glucose.

According to one embodiment, the collection volume 100 and chemically treated strip 102 are integrally formed, and are disposable. According to another embodiment, the chemically treated strip 102 is adhered to the collection volume 100, either or both of which may be disposed of after use. According to yet another embodiment, the strip 102 is suspended in the interior of the collection volume 100 by a fastening mechanism (not depicted in FIG. 1). According to yet another embodiment, the strip 102 is fashioned as a dipstick, and is later interfaced (e.g., inserted into) with a reader, which observes the change of state of the various pads 104 thereon.

Although the particular embodiment described herein discusses determining the chemical composition of particular urine constituents by use of a chemically treated strip 102, it is understood that other techniques for determining urine composition exist, and these other techniques are contemplated herein. Other examples include detection of a change of state of the chemical strips by electrical transduction, mechanical transduction (e.g., a piezoelectric biosensor), acoustic transduction, and/or thermal transduction. The various embodiments of the system disclosed herein may usefully employ any suitable scheme for determining urine composition. Additionally, the chemically treated strip may be wholly absent, and one or more physical properties of the urine may be determined.

According to one embodiment, a set of detectors 106 is aligned with each of the pads 104 on the strip 100. Each detector 106 observes the state change exhibited by its corresponding pad 104. Thus, in the context of the embodiment in which the various pads 104 change color in proportion to the concentration of a given urine constituent, the detectors 106 may be embodied as photosensitive elements. According to one embodiment, the elements exhibit a voltage or current in proportion to intensity of incident light of a given wavelength. According to another embodiment, an optical filter is interposed between each photosensitive element and the pad 104, so as to permit passage of wavelengths corresponding to the pad 104 to be observed. Thus, for example, given a pad 104 intended to exhibit various shades or intensities of the color blue in response to the concentration of a given urine constituent, the optical filter exhibits a passband centered approximately at a wavelength of 475 nm (i.e., the wavelength corresponding to blue light). Consequently, only blue light passes through the optical filter and is incident upon the photosensitive element. The element responds by generating a current or voltage indicative of the shade or intensity of the color of the pad, thereby indicating the concentration of a given constituent within the urine sample.

The detectors 106 are coupled to a controller 112, so that the data generated by the detectors 106 may be operated upon, analyzed, and/or transmitted via a network to a remote computer 122. The controller 112, analytical operations, and remote computer are discussed in further detail below.

According to one embodiment, a source of electromagnetic radiation (not depicted in FIG. 1) may be configured to irradiate the urine sample during reading of the pads 104. According to one embodiment, the source of electromagnetic radiation is disposed opposite the chemically treated strip 102.

The system may also include a wave emitter 108. The emitter 108 propagates a wave through the urine sample, whereupon the wave is received by a detector 110. The wave generated by the emitter 108 may be electromagnetic and/or acoustic. The detector 110 is arranged to receive the wave generated by the emitter. By virtue of passage through the urine, the wave is altered in known relation to a given physical and/or chemical characteristic of the urine. The detector 110 receives the wave and delivers one or more data values indicative of the signal to its output (discussed below). For example, the detector 110 may deliver values indicative of the amplitude, pulse delay, and/or phase shift exhibited by the received wave.

By generation of an acoustic signal, physical characteristics, such as specific gravity of the urine, may be determined. By generation of an electromagnetic signal, physical characteristics, such as overall color of the urine and/or refractive index of the urine, may be determined. According to one embodiment, the emitter 108 generates an electric signal that is received by the detector 110. The conductivity of the urine is revealed by the current or voltage level witnessed by the detector 110.

The information developed by the detectors 106 and 110 are delivered to a controller 112. According to one embodiment, the controller 112 includes a processor in communication with a memory, and an input/output (I/O) interface for coupling with detectors 106 and 110. For example, the controller 112 may be embodied as a computer or handheld wireless device, with appropriate interface circuitry for interaction with the various detectors 106 and 110. The controller 112 also includes a network interface for interaction with a network 114. For example, as shown in FIG. 1, the controller 112 may include a wireless network interface that permits interaction with a wireless access point 116. Alternatively, the controller 112 may include a network interface for interaction with a wired network, such as a local area network or the telephone network.

The controller 112 may be embodied as more than one device. For example, the detectors 106 for the chemically treated strip 102 may communicate with a first controller (e.g., computer or wireless device), the detector 110 for the emitter may communicate with a second controller, a blood analyzer 118 with a third controller, and a scale 120 with a fourth controller (the blood analyzer 118 and scale 120 are discussed below). Whether the controller 112 is embodied as one device or as more than one device, the system provides an interface for each of the devices/detectors 106, 110, 118, and 120 coupled thereto, so that the data developed by the devices/detectors 106, 110, 118, and 120 can be communicated via a network 114 to a remote computer 122, for storage in a database 124. Thus, the data from each of the detectors/devices 106, 110, 118, and 120 may be commingled and analyzed as a unit. This is discussed in greater detail below.

According to some embodiments, the system may include a blood analyzer 118. The blood analyzer 118 determines the concentration of various constituents of the blood. According to some embodiments, the blood analyzer 118 determines the blood concentration of the urine constituents measured by the chemically treated strip 102. Thus, for various constituents, the system determines both blood and urine concentration.

According to some embodiments, the system includes a scale 120. The scale 120 obtains weight measurements of a patient.

The system of FIG. 1 may be used periodically. For example, the system may be used on a daily basis by a patient. The patient may, for example, provide a urine sample to the system each morning for analysis via the chemically treated strip 102 and detectors 106 and 110. The patient may also weigh himself with scale 120, and may provide blood to the blood analyzer 118 for analysis thereof. The data from each of these detectors/devices 106, 110, 118, and 120 is then obtained by the controller 112, and communicated via the network 114 to a remote computer 122, and stored in a database 124.

The patient may have a pacemaker or other cardiac rhythm management device 126 implanted in his body. As used herein, the term "pacemaker" refers to cardiodefibrillators, pacemakers, CRT devices, congestive heart failure (CHF) devices, and any other device that delivers electrical pulses to the heart. According to some embodiments, the pacemaker 126 is configured to obtain baseline transthoracic impedance measurements from time to time (e.g., on a daily basis). The pacemaker 126 communicates the transthoracic impedance measurements to the controller 112, for subsequent communication to the remote computer 122 via the network 114. According to some embodiments, the pacemaker 126 communicates directly with the wireless access point 116. According to yet other embodiments, the pacemaker 126 communicates with a device (not depicted) that forwards the pacemaker data (e.g., baseline transthoracic impedance data) to the remote computer 122.

By virtue of all of the various detectors 106 and 110 and devices 118, 120, and 126 communicating their data through the network 114, an agglomerated data set is created and maintained in the database 124. The agglomerated data set may be manipulated and analyzed as shown generally in FIG. 2.

Figure 2:
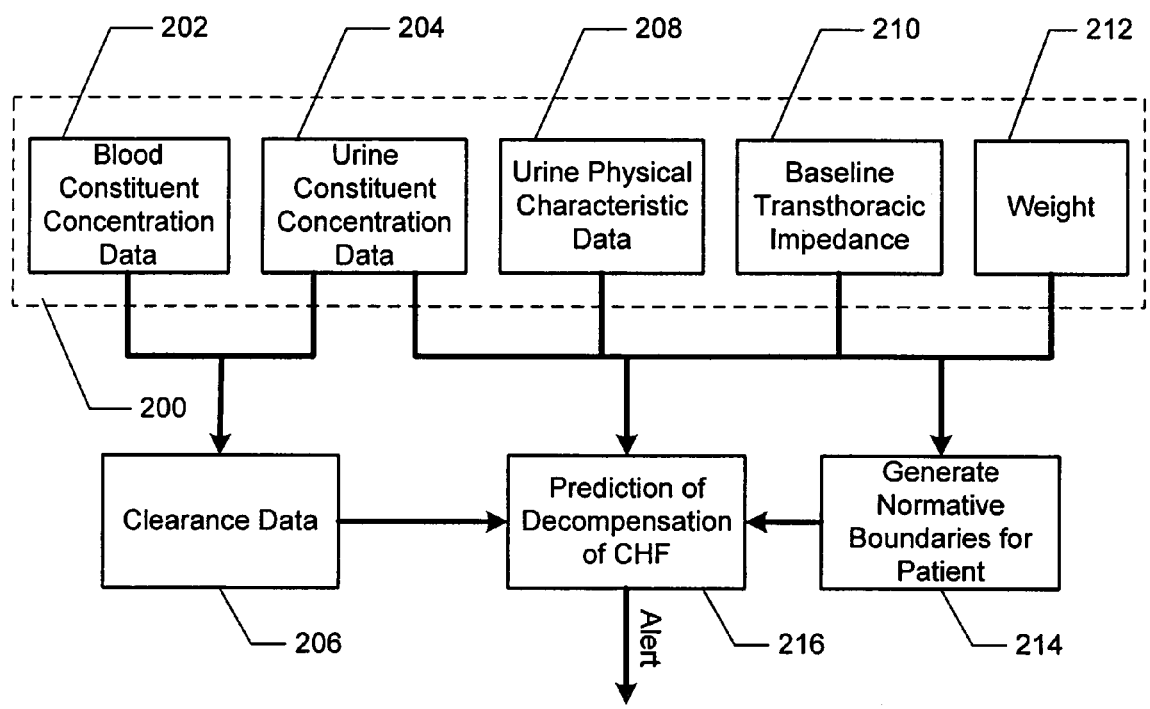
FIG. 2 depicts an exemplary embodiment of various data and modules operating thereupon to detect decompensation of heart failure and to track renal function generally.

FIG. 2 depicts the agglomerated data set 200 and exemplary manipulations and analyses that may be performed thereupon. As can be seen from FIG. 2, the agglomerated data set 200 (generated from the system of FIG. 1) includes blood constituent data 202, urine constituent data 204, data describing physical characteristics of the urine 208, baseline transthoracic impedance data 210, and weight 212. The agglomerated data set 200 may contain other data as well, such as other data developed by the pacemaker 126 (e.g., event markers, respiration data, heart sounds, etc.). Also, the agglomerated data set 200 may contain a subset of the any of the aforementioned data types (e.g., the agglomerated data set 200 may exclude blood constituent data 202, or may exclude baseline transthoracic impedance data 210, etc.).

According to one embodiment, the blood constituent concentration data 202 and urine constituent concentration data 204 are manipulated by a clearance data calculation module 206, so as to calculate the clearance rate exhibited by the patient with respect to various constituents. For example, the clearance data calculation module 206 may be embodied as software executed upon the remote computer 122 (or any other computer having access to the database 124), and according to one embodiment, functions as shown in FIG. 3.

Figure 3:
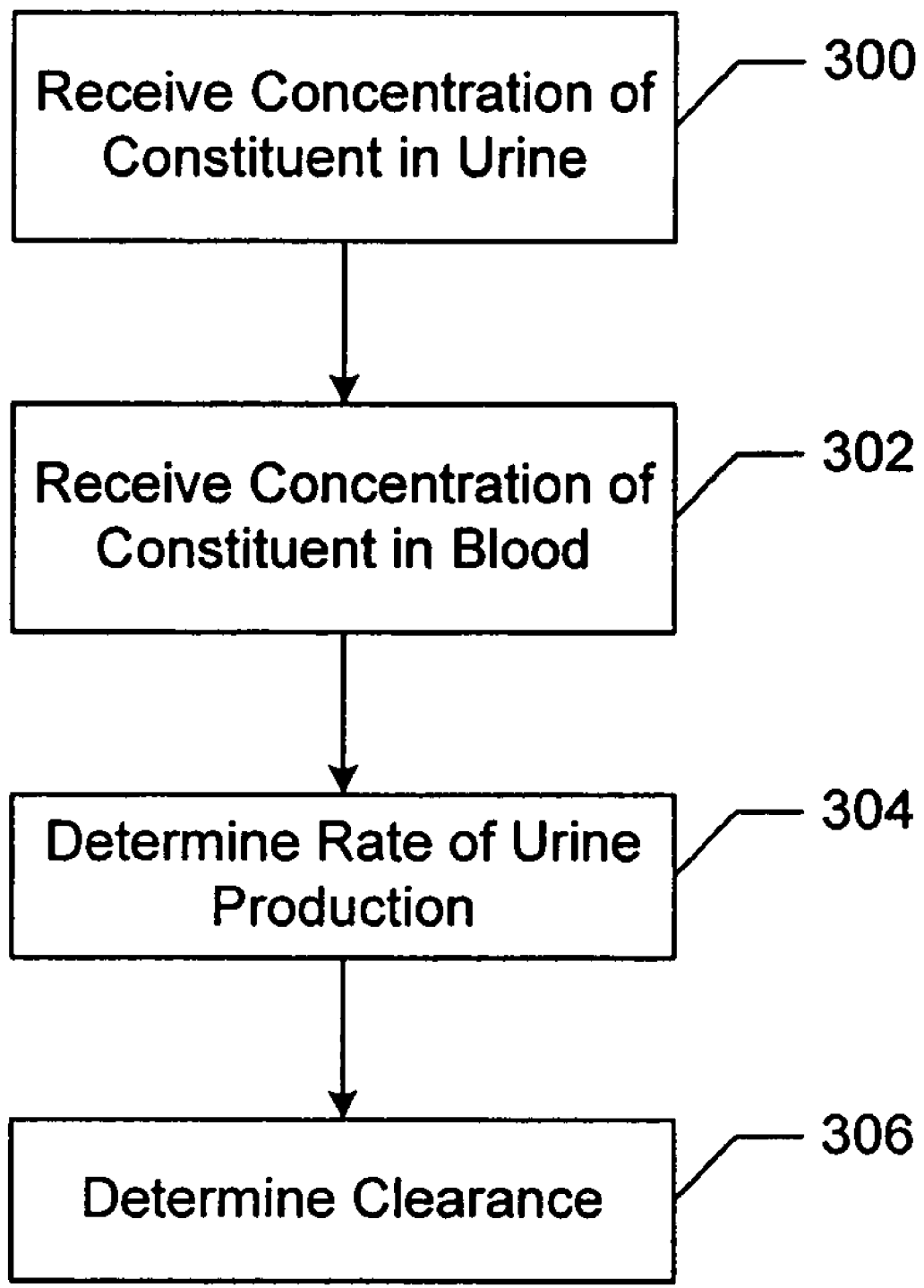
FIG. 3 depicts an exemplary embodiment of a method for determining the clearance rate exhibited by a patient for a given substance.

Turning to FIG. 3, the clearance data calculation module 206 commences its operation by receiving data describing the concentration of a particular constituent in the patient's urine (operation 300), $C_u$. This sort of data is collected from the detectors 106 corresponding to the various pads 104 on the strip 106, for example.

The clearance data calculation module 206 also receives data describing the concentration of the aforementioned particular constituent in the patient's blood (operation 302), $C_b$. This sort of data is collected from the blood analyzer device 118, for example.

In operation 304, the rate of urine production exhibited by the patient is determined. The rate of urine production may be determined in various ways. One example follows. The patient may use the scale 120 to weigh himself prior to and following urination, thereby determining the weight of the urine produced since his last occasion of urination. Alternatively, the patient may urinate into a container (e.g., a bag), and subsequently weigh the container to determine the weight of the urine. The weight of the urine may be divided by the density of the urine, thereby obtaining the volume of the urine. (The density of the urine may be obtained from the detector 110 corresponding to the emitter 108, per embodiments of the system in which the emitter 108 propagates an acoustic wave through the urine sample, for example.) The volume of the urine may be divided by the span of time since the patient last urinated, thereby arriving at the rate of urine production, R.

Finally, as shown in operation 306, the clearance rate exhibited by the patient for the aforementioned particular constituent may be determined. For example, the clearance may be calculated by the following equation:

$$\text{clearance} = R[C_u/C_b],$$

where R represents the rate of urine production exhibited by the patient, $C_u$ represents the concentration of a given constituent found in the patient's urine, and $C_b$ represents the concentration of the given constituent found in the patient's blood plasma.

Figure 4:
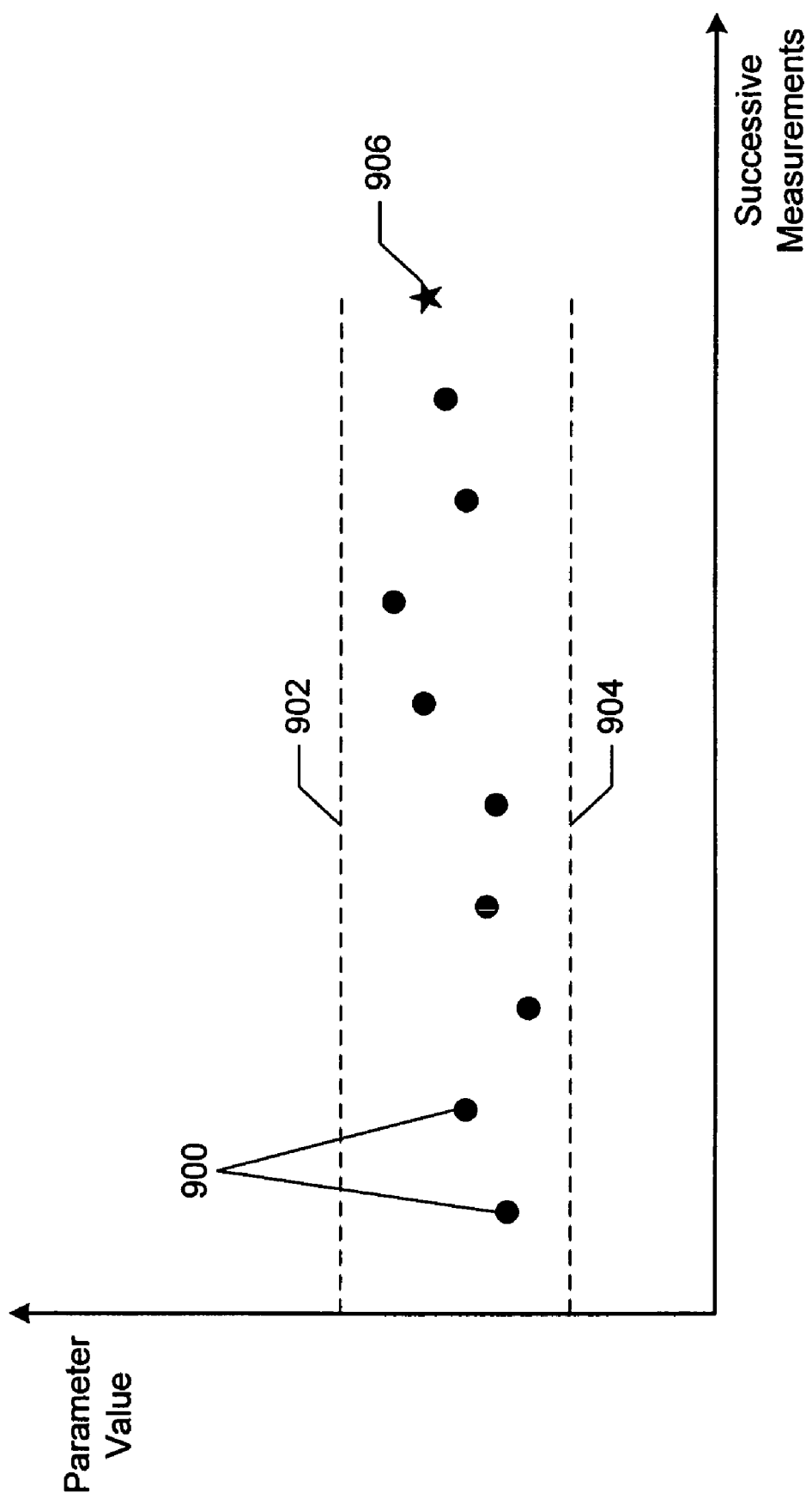
FIG. 4 depicts a plurality of consecutive measurements of a particular parameter, and shows upper and lower boundaries for the particular parameter.

Returning to FIG. 2, it can be seen that, according to some embodiments, a boundary generation module 214 operates upon the urine constituent data 204, the data describing physical characteristics of the urine 208, baseline transthoracic impedance data 210, and weight data 212. According to some embodiments, the boundary generation module 214 also acts upon the blood constituent data 202. The boundary generation module 214 generates one or more boundaries for each parameter within the agglomerated data set. The one or more boundaries indicate the "normal" range for a given parameter. For example, turning to FIG. 4, therein is depicted a set of N=9 past measurements 400 of a particular parameter, only two of which are labeled with reference numeral 400. Also depicted therein are an upper boundary 402 and a lower boundary 404. The boundaries 402 and 404 are calculated by the boundary generation module 214, based upon previous measurements of the given parameter. For example, in the case depicted in FIG. 4, the boundaries are calculated on the basis of the previous N=9 measurements of the parameter. It is understood that N may take on other values, as appropriate for the given tracked parameter (e.g., N=30, 50, 60, 90, or 100). The boundaries are calculated to identify a normal range for the patient (i.e., the span of values greater than the lower boundary 404 and less than the upper boundary 402). Each new measurement of the particular parameter is compared to the upper and lower boundaries 402 and 404, to determine if the new measurement is normal, given the historical data of the patient. For example, new measurement 406 is compared to the upper and lower boundaries 402 and 404 to determine whether the new measurement is within the normal range (in the example shown in FIG. 4, the new measurement 406 is within the normal range). A parameter measurement falling outside of the boundaries may be regarded as abnormal for the patient, meaning that it may indicate an increased probability of impending decompensation of heart failure for the particular patient. The parameters for which boundaries may be generated include, without limitation, urine concentration of protein, sodium, uric acid, urea, creatinine, leukocyte estrase, nitrites, bilirubin, ketones, heart failure medication, and/or glucose, blood concentration of protein, sodium, uric acid, urea, creatinine, leukocyte estrase, nitrites, bilirubin, ketones, heart failure medication, and/or glucose, clearance rates for urea, creatinine, heart failure medication, and/or glucose, urine color, urine darkness, urine density, urine conductivity, refractive index of urine, baseline transthoracic impedance, any parameter or data measured by or generated by a cardiac rhythm management device, patient weight, and the ratio of urine sodium to urine creatinine.

Figure 5:
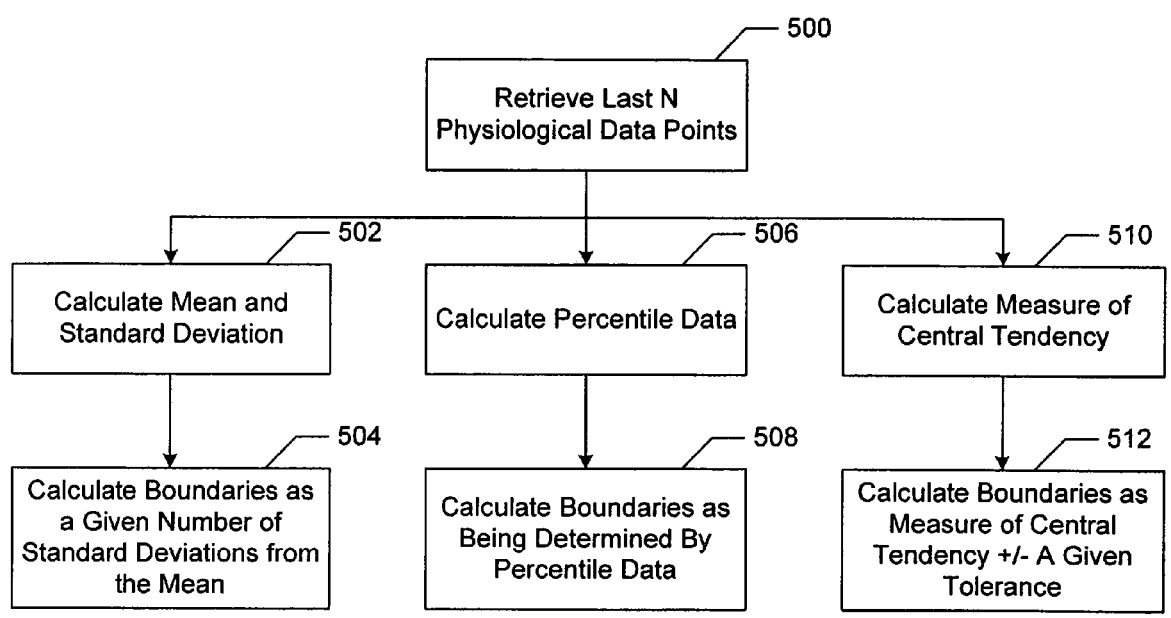
FIG. 5 depicts exemplary embodiments of methods for determining upper and/or lower boundaries for a given parameter.

FIG. 5 depicts exemplary methods by which the boundaries 402 and 404 may be determined for a given parameter. Initially, a set of N past measurements for a given parameter are retrieved from the database 124, as shown in operation 500. Thereafter, the set of N measurements may be operated upon as shown in operations 502-512 to determine the boundaries. For example, as shown in operation 502, the mean, $\mu$, and standard deviation, $\sigma$, of the N measurements may be determined. Then, as shown in operation 504, the boundaries may be determined as a particular number of standard deviations from the mean:

$$\text{boundaries}=\mu+/-k\sigma,$$

where k represents a coefficient chosen for determining the number of standard deviations the boundaries are away from the mean.

Alternatively, the set of N past measurements may be analyzed for determination of particular values at which chosen percentiles fall, as shown in operation 506. For example, the set of N past measurements may be analyzed to determine the values at which the 10th percentile falls and the 90th percentile falls (i.e., a value beneath which 10% of the past N measurements fall, and a value beneath which 90% of the past N measurements fall). Then, as shown in operation 508, the boundaries may be set at those values, or at another value that is a function of the determined percentile values.

Still alternatively, the set of N past measurements may be analyzed for determination of a measurement of their central tendency (e.g., arithmetic mean, geometric mean, median, etc.), as shown in operation 510. Then, the boundaries may be determined by as:

$$\text{boundaries}=\text{central tendency}+/-C,$$

where C represents a chosen tolerance for determining the difference between the boundaries and the measure of central tendency of the last N measurements of the given parameter.

Figure 6:
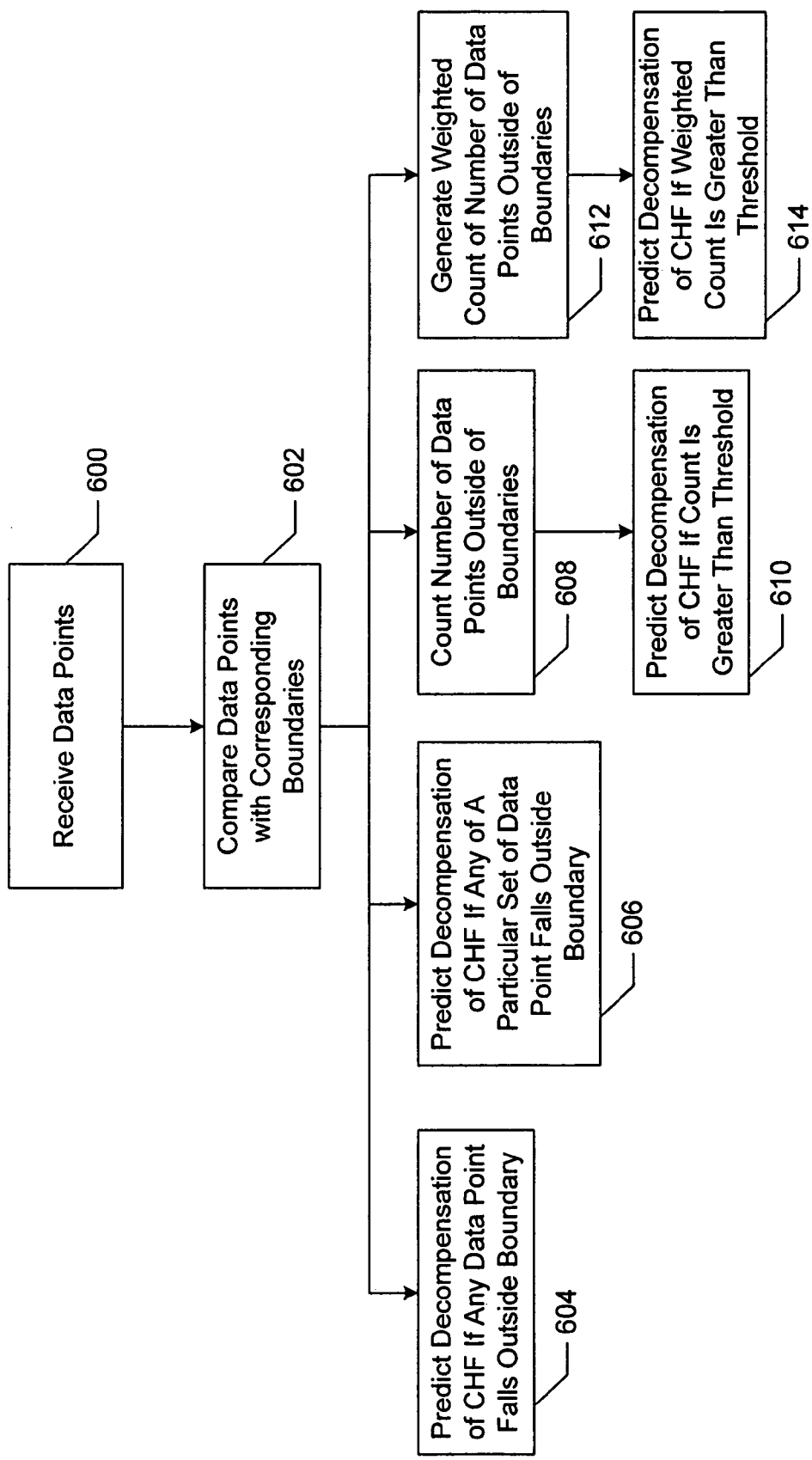
FIG. 6 depicts exemplary embodiments of methods of detecting impending decompensation of heart failure.

Returning to FIG. 2, it can be seen that the system also includes a CHF decompensation detection module 216. The CHF decompensation detection module 216 utilizes the various boundaries generated by the boundary generation module 214, in order to detect decompensation of heart failure. For example, upon the reception of a recent measurement of a parameter (operation 600 in FIG. 6), the boundaries for the parameter are obtained from the boundary generation module. Then, the measurement is compared with the boundaries, as shown in operation 602. According to one embodiment, if any new measurement falls outside of the boundaries (i.e., is abnormal for the patient), then decompensation of heart failure is detected, as shown in operation 604.

According to another embodiment, certain parameters are deemed critical to the determination of decompensation of CHF. Thus, if any of the critical parameters fall outside of their respective boundaries, then decompensation of CHF is detected, as shown in operation 606.

According to yet another embodiment, the CHF decompensation detection module 216 counts the number of parameters falling outside of their respective boundaries (operation 608). If the counted number of abnormal parameters exceeds a threshold, then decompensation of CHF is detected.

According to yet another embodiment, each parameter is assigned a score. If a given parameter falls outside of its boundary, then a running tally is incremented by the score assigned to the parameter (operation 610). If the running tally exceeds a threshold, then decompensation of CHF is detected, as shown in operation 612.

According to some embodiments, upon detection of impending decompensation of a given patient's heart failure, the remote computer 122 may access the database 124 to obtain contact information (e.g., an e-mail address, pager number, etc.) for one or more health care providers corresponding to the particular patient. The system 122 then uses the contact information to transmit an alert to the health care provider. The alert informs the health care provider of the particular patient for which impending decompensated heart failure has been detected.

The above described devices, system and methods are described with respect to an advanced patient management system configured to collect patient-specific information (urinalysis information, weight information, blood concentration information, etc.), store and collate the information, and generate actionable recommendations to enable the predictive management of patients. The advanced patient management system is also configured to leverage a remote communications infrastructure to provide automatic device follow-ups to collect data, coordinate therapy, and to determine if remote devices are functioning properly. The term "patient" is used herein to mean any individual from whom information is collected. The term "caregiver" is used herein to mean any provider of services, such as health care providers including, but not limited to, nurses, doctors, and other health care provider staff.

Figure 7:
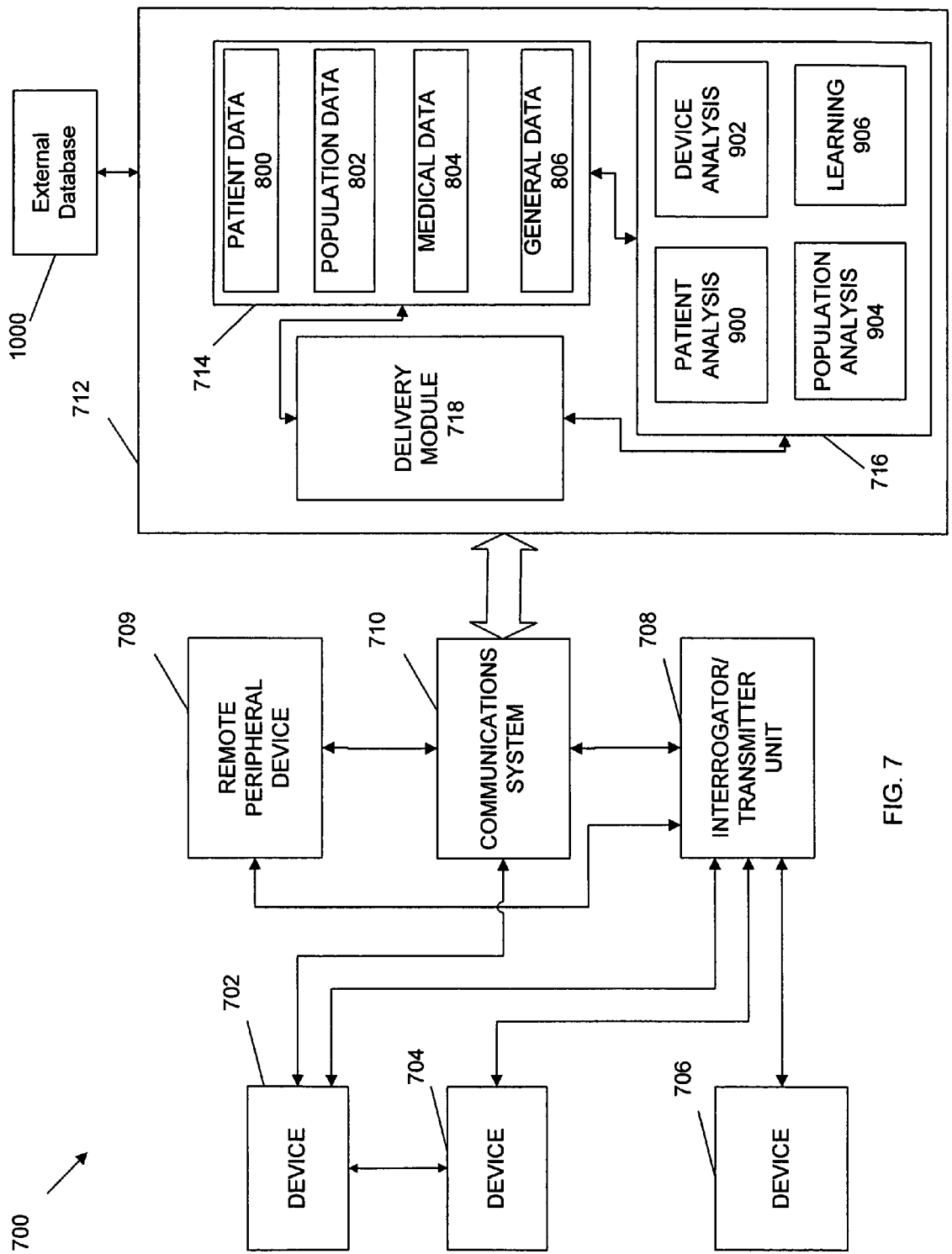
FIG. 7 depicts an examplary embodiment of an advanced patient management system.

FIG. 7 illustrates an example advanced patient management system 700 made in accordance with the present invention. Advanced patient management system 700 generally includes the following components: one or more devices 702, 704, and 706, one or more interrogator/transceiver units 708, a communication system 710, one or more remote peripheral devices 709, and a host 712.

In the description that follows, the advanced patient management system is describe generically, not making specific reference to the devices descirbed with reference to FIGS. 1-6. It is to be appreciated that the devices identified by reference numerals 702, 704, and 706 generally correspond, for example, to sensors/analyzers/scale/pacer 106, 110, 118, 120, and 126 in FIG. 1. It is to be appreciated that external database 1000 generall corresponds with data store 124, and that host 712 generally corresponds with server 124. Further, it is to be appreciated that interrogator/transmitter unit 708 generally corresponds with controller 112. Thus, what follows is a broad description of the communication capacity, processing capacity, processing sites, storage capacity, and storage sites of the system and methods described with reference to FIGS. 1-6.

Each component of the advanced patient management system 700 can communicate using the communication system 710. Some components may also communicate directly with one another. For example, devices 702 and 704 may be configured to communicate directly with one another. The various components of the example advanced patient management system 700 illustrated herein are described below.

I. Devices

Devices 702, 704, and 706 can be implantable devices or external devices that may provide one or more of the following functions with respect to a patient: (1) sensing, (2) data analysis, and (3) therapy. For example, in one embodiment, devices 702, 704, and 706 are either implanted or external devices used to measure a variety of physiological, subjective, and environmental conditions of a patient using electrical, mechanical, and/or chemical means. The devices 702, 704, and 706 can be configured to automatically gather data or can require manual intervention by the patient. The devices 702, 704, and 706 can be configured to store data related to the physiological and/or subjective measurements and/or transmit the data to the communication system 710 using a variety of methods, described in detail below. Although three devices 702, 704, and 706 are illustrated in the example embodiment shown, more or fewer devices may be used for a given patient.

The devices 702, 704, and 706 can be configured to analyze the measured data and act upon the analyzed data. For example, the devices 702, 704, and 706 are configured to modify therapy or provide alarm indications based on the analysis of the data.

In one embodiment, devices 702, 704, and 706 also provide therapy. Therapy can be provided automatically or in response to an external communication. Devices 702, 704, and 706 are programmable in that the characteristics of their sensing, therapy (e.g., duration and interval), or communication can be altered by communication between the devices 702, 704, and 706 and other components of the advanced patient management system 700. Devices 702, 704, and 706 can also perform self-checks or be interrogated by the communication system 710 to verify that the devices are functioning properly. Examples of different embodiments of the devices 702, 704, and 706 are provided below.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance.

A heart rhythm sensor, typically found in a pacemaker or defibrillator, is one example of an implantable device. In the heart, an electrical wave activates the heart muscle just prior to contraction. As is known in the art, electrical circuits and lead-wires transduce the heart's activation event and reject other, non-essential electrical events. By measuring the time interval between activation events, the heart rhythm can be determined. A transthoracic impedance sensor is another example of a sensor in an implantable device. During the respiratory cycle, large volumes of air pass into and out of the body. The electrical resistance of the thorax changes markedly as a result of large differences in conductivity of air and body tissues. The thoracic resistance can be measured during respiration and converted into a measurable electrical signal (i.e., impedance) so that breathing rate and profile can be approximated. Implantable devices can also sense chemical conditions, such as glucose levels, blood oxygen levels, etc. Further, the advanced patient management system 700 may utilize other implantable devices as well that provide physiological measurements of the patient, such as drug pumps, neurological devices (e.g., stimulators), oxygen sensors, etc.

Derived measurements can also be determined from the implantable device sensors. For example, a sleep sensor can rely on measurements taken by an implanted accelerometer that measures body activity levels. The sleep sensor can estimate sleeping patterns based on the measured activity levels. Other derived measurements include, but are not limited to, a functional capacity indicator, autonomic tone indicator, sleep quality indicator, cough indicator, anxiety indicator, and cardiovascular wellness indicator for calculating a quality of life indicator quantifying a patient's overall health and well-being.

Devices 702, 704, and 706 can also be external devices, or devices that are not implanted in the human body, that are used to measure physiological data. Such devices include a multitude of devices to measure data relating to the human body, such as temperature (e.g., a thermometer), blood pressure (e.g., a sphygmomanometer), blood characteristics (e.g., glucose levels), body weight, physical strength, mental acuity, diet, heart characteristics, and relative geographic position (e.g., a Global Positioning System (GPS)).

Devices 702, 704, and 706 can also be environmental sensors. The devices can be placed in a variety of geographic locations (in close proximity to patient or distributed throughout a population) and record non-patient specific characteristics such as, but not limited to, temperature, air quality, humidity, carbon monoxide level, oxygen level, barometric pressure, light intensity, and sound.

One or more of the devices 702, 704, and 706 (for example, device 706) may be external devices that measure subjective or perceptive data from the patient. Subjective data is information related to a patient's feelings, perceptions, and/or opinions, as opposed to objective physiological data. For example, the "subjective" devices can measure patient responses to inquiries such as "How do you feel?" and "How is your pain?" The device can prompt the patient and record subjective data from the patient using visual and/or audible cues. For example, the patient can press coded response buttons or type an appropriate response on a keypad. Alternatively, subjective data may be collected by allowing the patient to speak into a microphone and using speech recognition software to process the subjective data.

In one example embodiment, the subjective device presents the patient with a relatively small number of responses to each question posed to the patient. For example, the responses available to the patient may include three faces representing feelings of happiness, nominalness, and sadness. Averaged over time, a trend of a patient's well being will emerge with a finer resolution than the quanta of the three responses.

The subjective data can be collected from the patient at set times, or, alternatively, collected whenever the patient feels like providing subjective data. The subjective data can also be collected substantially contemporaneously with physiological data to provide greater insight into overall patient wellness. The subjective device 706 can be any device that accepts input from a patient or other concerned individual and/or provides information in a format that is recognizable to the patient. Device 706 typically includes a keypad, mouse, display, handheld device, interactive TV, cellular telephone or other radio frequency ("RF") communications device, cordless phone, corded phone, speaker, microphone, email message, or physical stimulus.

The advanced patient management system 700 may also include one or more remote peripheral devices 709. The remote peripheral device 709 may include, for example and without limitation, cellular telephones, pagers, PDA devices, facsimiles, remote computers, printers, video and/or audio devices, etc. The remote peripheral device 709 can communicate using wired or wireless technologies and may be used by the patient or caregiver to communicate with the communication system 710 and/or the host 712. For example, the remote peripheral device 709 can be used by the caregiver to receive alerts from the host 712 based on data collected from the patient and to send instructions from the caregiver to either the patient or other clinical staff. In another example, the remote peripheral device 709 is used by the patient to receive periodic or real time updates and alerts regarding the patient's health and well-being.

II. Interrogator/Transceiver Unit

The example advanced patient management system 700 includes one or more interrogator/transceiver units ("ITUs"), such as ITU 708. The ITU 708 includes an interrogator module for sending and receiving data from a device, such as devices 702, 704, and 706, a memory module for storing data, and a transceiver module for sending and receiving data to and from other components of the APM system 700. The transceiver module may also operate as an interrogator of the devices 702, 704 and 706. The ITU 708 also includes a power module that provides power.

The ITU 708 may perform one or more of the following functions: (1) data storage; (2) data analysis; (3) data forwarding; (4) patient interaction; (5) patient feedback; and (6) data communications. For example, the ITU 708 may facilitate communications between the devices 702, 704, and 706 and the communication system 710. The ITU 708 can, periodically or in real-time, interrogate and download into memory clinically relevant patient data from the devices 702, 704, and/or 706. This data includes, in the cardiac sensor context, for example, P and R-wave measurements, pacing, shocking events, lead impedances, pacing thresholds, battery voltage, capacitor charge times, ATR episodes with electrograms, tachycardia episodes with electrograms, histogram information, and any other clinical information necessary to ensure patient health and proper device function. The data is sent to the ITU 708 by the devices 702, 704, and 706 in real-time or periodically uploaded from buffers in the devices.

The ITU 708 may also allow patient interaction. For example, the ITU 708 may include a patient interface and allow the patient to input subjective data. In addition, the ITU 708 may provide feedback to the patient based on the data that has been analyzed or based on information communicated by the communication system 710.

In another embodiment, the ITU 708 includes a telemetry link from the devices to a network that forms the basis of a wireless LAN in the patient's home. The ITU 708 systematically uploads information from the devices 702, 704, and/or 706 while the patient is sleeping, for example. The uploaded data is transmitted through the communication system 710 or directly to the host 712. In addition, in one embodiment the ITU 708 functions in a hybrid form, utilizing wireless communication when available and defaulting to a local wireless portal or a wired connection when the wireless communication becomes unavailable.

Some devices, such as legacy implanted cardiac rhythm management ("CRM") devices, communicate via an internal telemetry transceiver that communicates with an external programmer. The communication range of such devices is typically 1 to 4 inches. ITU 708 may include a special short-range interrogator that communicates with a legacy device.

When the ITU 708 uses radio frequency to communicate with the devices 702, 704, 706, the ITU 708 may be in the form of a small device that is placed in an inconspicuous place within the patient's residence. Alternatively, the ITU 708 may be implemented as part of a commonly-used appliance in the patient's residence. For example, the ITU may be integrated with an alarm clock that is positioned near the patient's bed. In another embodiment, the ITU may be implemented as part of the patient's personal computer system. Other embodiments are also possible.

In another embodiment, the ITU 708 may comprise a hand-held device such as a PDA, cellular telephone, or other similar device that is in wireless communication with the devices 702, 704, and 706. The hand-held device may upload the data to the communication system 710 wirelessly. Alternatively, the hand-held device may periodically be placed in a cradle or other similar device that is configured to transmit the data to the communication system 710.

In one embodiment, the ITU 708 can perform analysis on the data and provide immediate feedback, as well as perform a variety of self-diagnostic tests to verify that it is functioning properly and that communication with the communication system 710 has not be compromised. For example, the ITU 708 can perform a diagnostic loop-back test at a time set by the host 712, which involves sending a request through the communication system 710 to the host 712. The host 712 can then reply with a response back through the communication system 710 to the ITU 708. If a specific duration elapses before the ITU 708 receives the response or the ITU 708 receives an unexpected response, or if the host 712 does not receive the diagnostic test communication, the ITU 708 can provide indications that the system is not functioning properly and the host 712 can alert an operator that there may be compromised communications with that specific ITU 708. For example, if wireless communications between the ITU 708 and the communication system 710 have been interrupted, and the ITU 708 performs a self-diagnostic test that fails, the ITU 708 may alert the patient so that corrective action may be taken. The alert can take the form of a sound or a visual and/or audible annunciator to alert the patient that communication has been interrupted. In another embodiment, the ITU 708 can automatically fail-back to a wired system to communicate with the communication system 710 and perform the same communications compromise checks.

In other embodiments of the advanced patient management system 700, the ITU 708 function can be integrated into devices 702, 704, and 706, so that the devices can communicate directly with the communication system 710 and/or host 712. The devices 702, 704 and 706 can incorporate multimode wireless telecommunications such as cellular, BLUETOOTH, or IEEE 802.11B to communicate with the communication system 710 directly or through a local wireless to a wired portal in the patients' home. For example, device 702 may include a miniature cellular phone capable of wirelessly uploading clinical data from the device on a periodic basis. This is particularly advantageous for devices that are mobile (e.g., an implanted device in a patient that is traveling).

To conserve the energy of the devices 702, 704, and 706, particularly when the devices (e.g., device 702) are configured to communicate directly with the communication system 710 without using an ITU 708, in one example embodiment the devices are configured to communicate during a given duty cycle. For example, the device 702 can be configured to communicate with the communication system 710 at given intervals, such as once a week. The device 702 can record data for the time period (e.g., a week) and transmit the data to the communication system 710 during the portion of the cycle that transmission is active and then conserve energy for the rest of the cycle. In another example, the device 702 conserves energy and only communicates with the communication system 710 when an "interesting" event, such as a heart arrhythmia, has occurred. In this manner, device 702 can communicate directly with the communication system 710 and/or host 712 without requiring an ITU 708, while conserving the energy of the device by communicating only during a given duty cycle.

The interrogation rate of the ITU 708 can be varied depending on disease state and other relevant factors. In addition, the devices 702, 704, and 706 can be configured to "wake up" frequently (e.g., once every couple minutes) to provide the ITU 708 an access window for the ITU 708 to provide commands to the devices 702, 704, and 706, as well as upload data from the devices.

If multiple devices, such as devices 702, 704, and 706, are provided for a given patient, each device may include its own means for communicating with the ITU 708 or communication system 710. Alternatively, a single telemetry system may be implemented as part of one of the devices, or separate from the devices, and each device 702, 704, and 706 can use this single telemetry system to communication with the ITU 708 or the communication system 710.

In yet another embodiment, the devices 702, 704, and 706 include wires or leads extending from devices 702, 704, and 706 to an area external of the patient to provide a direct physical connection. The external leads can be connected, for example, to the ITU 708 or a similar device to provide communications between the devices 702, 704, and 706 and the other components of the advanced patient management system 700.

The advanced patient management system 700 can also involve a hybrid use of the ITU 708. For example, the devices 702, 704, and 706 can intelligently communicate via short-range telemetry with the ITU when the patient is located within the patient's home and communicate directly with the communication system 710 or host 712 when the patient is traveling. This may be advantageous, for example, to conserve battery power when the devices are located near an ITU.

III. Communication System

Communication system 710 provides for communications between and among the various components of the advanced patient management system 700, such as the devices 702, 704, and 706, host 712, and remote peripheral device 709.

IV. Host

The example host 712 includes a database module 714, an analysis module 716, and a delivery module 718 (see FIG. 7). Host 712 preferably includes enough processing power to analyze and process large amounts of data collected from each patient, as well as to process statistics and perform analysis for large populations. For example, the host 712 may include a mainframe computer or multi-processor workstation. The host 712 may also include one or more personal computer systems containing sufficient computing power and memory. The host 712 may include storage medium (e.g., hard disks, optical data storage devices, etc.) sufficient to store the massive amount of high-resolution data that is collected from the patients and analyzed.

The host 712 may also include identification and contact information (e.g., IP addresses, telephone numbers, or a product serial number) for the various devices communicating with it, such as ITU 708 and peripheral device 709. For example, each ITU 708 is assigned a hard-coded or static identifier (e.g., IP address, telephone number, etc.), which allows the host 712 to identify which patient's information the host 712 is receiving at a given instant. Alternatively, each device 702, 704, and 706 may be assigned a unique identification number, or a unique patient identification number may be transmitted with each transmission of patient data.

When a device is first activated, several methods may be used to associate data received by the advanced patient management system 700 with a given patient. For example, each device may include a unique identification number and a registration form that is filled out by the patient, caregiver, or field representative. The registration form can be used to collect the necessary information to associate collected data with the patient. Alternatively, the user can logon to a web site to allow for the registration information to be collected. In another embodiment, a barcode is included on each device that is scanned prior to or in conjunction deployment of the device to provide the information necessary to associate the recorded data with the given patient.

Referring again to FIG. 7, the example database module 714 includes a patient database 800, a population database 802, a medical database 804, and a general database 806, all of which are described further below.

The patient database 800 includes patient specific data, including data acquired by the devices 702, 704, and 706. The patient database 800 also includes a patient's medical records. The patient database 800 can include historical information regarding the devices 702, 704, and 706. For example, if device 702 is an implantable cardioverter defibrillator (ICD), the patient database 800 records the following device information: P and R measurements, pacing frequency, pacing thresholds, shocking events, recharge time, lead impedance, battery voltage/remaining life, ATR episode and EGMs, histogram information, and other device-specific information. The information stored in the database 800 can be recorded at various times depending on the patient requirements or device requirements. For example, the database 800 is updated at periodic intervals that coincide with the patient downloading data from the device. Alternatively, data in the database 800 can be updated in real time. Typically, the sampling frequency depends on the health condition being monitored and the co-morbidities.

The population database 802 includes non-patient specific data, such as data relating to other patients and population trends. The population database 802 also records epidemic-class device statistics and patient statistics. The population database 802 also includes data relating to staffing by health care providers, environmental data, pharmaceuticals, etc.

The example medical database 804 includes clinical data relating to the treatment of diseases. For example, the medical database 804 includes historical trend data for multiple patients in the form of a record of progression of their disease (s) along with markers of key events.

The general database 806 includes non-medical data of interest to the patient. This can include information relating to news, finances, shopping, technology, entertainment, and/or sports. The general database 806 can be customized to provide general information of specific interest to the patient. For example, stock information can be presented along with the latest health information as detected from the devices 702, 704, and 706.

In another embodiment, information is also provided from an external source, such as external database 1000. For example, the external database 1000 includes external medical records maintained by a third party, such as drug prescription records maintained by a pharmacy, providing information regarding the type of drugs that have been prescribed for a patient.

The example analysis module 716 includes a patient analysis module 900, device analysis module 902, population analysis module 904, and learning module 906.

Patient analysis module 900 may utilize information collected by the advanced patient management system 700, as well as information for other relevant sources, to analyze data related to a patient and provide timely and predictive assessments of the patient's well-being. In performing this analysis, the patient device module 900 may utilize data collected from a variety of sources, include patient specific physiological and subjective data collected by the advanced patient management system 700, medical and historical records (e.g., lab test results, histories of illnesses, etc., drugs currently and previously administered, etc.), as well as information related to population trends provided from sources external to the advanced patient management system 700.

For example, in one embodiment, the patient analysis module 900 makes a predictive diagnosis of an oncoming event based on information stored in the database module 714. For example, the data continuously gathered from a device of a given patient at a heightened risk for a chronic disease event (such as de-compensations in heart failure) is analyzed. Based on this analysis, therapy, typically device-based or pharmaceutical, is then be applied to the patient either through the device or through clinician intervention.

In another example embodiment, the patient analysis module 900 provides a diagnosis of patient health status and predicted trend based on present and recent historical data collected from a device as interpreted by a system of expert knowledge derived from working practices within clinics. For example, the patient analysis module 900 performs probabilistic calculations using currently-collected information combined with regularly-collected historical information to predict patient health degradation.

In another example embodiment, the patient analysis module 900 may conduct pre-evaluation of the incoming data stream combined with patient historical information and information from patients with similar disease states. The pre-evaluation system is based on data derived from working clinical practices and the records of outcomes. The derived data is processed in a neural network, fuzzy logic system, or equivalent system to reflect the clinical practice. Further, the patient analysis module 900 may also provide means for periodic processing of present and historical data to yield a multidimensional health state indication along with disease trend prediction, next phase of disease progression co-morbidities, and inferences about what other possible diseases may be involved. The patient analysis module 900 may also integrate data collected from internal and external devices with subjective data to optimize management of overall patient health.

Device analysis module 902 analyzes data from the devices 702, 704, and 706 and ITU 708 to predict and determine device issues or failures. For example, if an implanted device 702 fails to communicate at an expected time, device analysis module 902 determines the source of the failure and takes action to restore the performance of the device 702. The device analysis module 902 may also perform additional deterministic and probabilistic calculations. For example, the device analysis module 902 gathers data related to charge levels within a given device, such as an ICD, and provides analysis and alerting functions based on this information if, for example, the charge level reaches a point at which replacement of the device and/or battery is necessary. Similarly, early degradation or imminent failure of implanted devices can be identified and proactively addressed, or at-risk devices can be closely monitored.

Population analysis module 904 uses the data collected in the database module 714 to manage the health of a population. For example, a clinic managing cardiac patients can access the advanced patient management system 700 and thereby obtain device-supplied advance information to predict and optimize resource allocation both as to immediate care and as a predictive metric for future need of practicing specialists. As another example, the spread of disease in remote populations can be localized and quarantined rapidly before further spread.

In one embodiment, population analysis module 904 trends the patient population therapy and management as recorded by the devices and directs health care resources to best satisfy the needs of the population. The resources can include people, facilities, supplies, and/or pharmaceuticals. In other embodiments, the population analysis module detects epidemics and other events that affect large population groups. The population analysis module 904 can issue alerts that can initiate a population quarantine, redirect resources to balance size of staffing with number of presenting population, and predict future need of qualified specialists.

The population analysis module 904 may utilize a variety of characteristics to identify like-situated patients, such as, for example, sex, age, genetic makeup, etc. The population analysis module 904 may develop large amounts of data related to a given population based on the information collected by the advanced patient management system 700. In addition, the population analysis module 904 may integrate information from a variety of other sources. For example, the population analysis module 904 may utilize data from public domain databases (e.g., the National Institute of Health), public and governmental and health agency databases, private insurance companies, medical societies (e.g., the American Heart Association), and genomic records (e.g., DNA sequences).

In one embodiment of the invention, the host 712 may be used as a "data clearinghouse," to gather and integrate data collected from the devices 702, 704, and 706, as well as data from sources outside the advanced patient management system 700. The integrated data can be shared with other interested entities, subject to privacy restrictions, thereby increasing the quality and integration of data available.

Learning module 906 analyzes the data provided from the various information sources, including the data collected by the advanced patient system 700 and external information sources. For example, the learning module 906 analyzes historical symptoms, diagnoses, and outcomes along with time development of the diseases and co-morbidities. The learning module 906 can be implemented via a neural network (or equivalent) system.

The learning module 906 can be partially trained (i.e., the learning module 906 may be implemented with a given set of preset values and then learn as the advanced patient management system functions) or untrained (i.e., the learning module 906 is initiated with no preset values and must learn from scratch as the advanced patient management system functions). In other alternative embodiments, the learning module 906 may continue to learn and adjust as the advanced patient management system functions (i.e., in real time), or the learning module 906 may remain at a given level of learning and only advanced to a higher level of understanding when manually allowed to do so.

In a neural network embodiment, new clinical information is presented to create new neural network coefficients that are distributed as a neural network knowledge upgrade. The learning module 906 can include a module for verifying the neural network conclusions for clinical accuracy and significance. The learning module can analyze a database of test cases, appropriate outcomes and relative occurrence of misidentification of the proper outcomes. In some embodiments, the learning module 906 can update the analysis module 716 when the analysis algorithms exceed a threshold level of acceptable misidentifications.

The example learning module 906 uses various algorithms and mathematical modeling such as, for example, trend and statistical analysis, data mining, pattern recognition, cluster analysis, neural networks and fuzzy logic. Learning module 906 may perform deterministic and probabilistic calculations. Deterministic calculations include algorithms for which a clear correlation is known between the data analyzed and a given outcome. For example, there may be a clear correlation between the energy left in a battery of an implantable device and the amount of time left before the battery must be replaced.

A probabilistic calculation involves the correlation between data and a given outcome that is less than 700 percent certain. Probabilistic determinations require an analysis of several possible outcomes and an assignment of probabilities for those outcomes (e.g., an increase in weight of a patient may, at a 25% probability, signal an impending de-compensation event and/or indicate that other tests are needed). The learning module 906 performs probabilistic calculations and selects a given response based on less than a 700% probability. Further, as the learning module 906 "learns" for previous determinations (e.g., through a neural network configuration), the learning module 906 becomes more proficient at assigning probabilities for a given data pattern, thereby being able to more confidently select a given response. As the amount of data that has been analyzed by the learning module 906 grows, the learning module 906 becomes more and more accurate at assigning probabilities based on data patterns. A bifurcated analysis may be performed for diseases exhibiting similar symptoms. As progressive quantities of data are collected and the understanding of a given disease state advances, disease analysis is refined where a former singular classification may split into two or more sub-classes.

In addition, patient-specific clinical information can be stored and tracked for hundreds of thousands of individual patients, enabling a first-level electronic clinical analysis of the patient's clinical status and an intelligent estimate of the patient's short-term clinical prognosis. The learning module 906 is capable of tracking and forecasting a patient's clinical status with increasing levels of sophistication by measuring a number of interacting co-morbidities, all of which may serve individually or collectively to degrade the patient's health. This enables learning module 906, as well as caregivers, to formulate a predictive medical response to oncoming acute events in the treatment of patients with chronic diseases such as heart failure, diabetes, pain, cancer, and asthma/COPD, as well as possibly head-off acute catastrophic conditions such as MI and stroke.

Delivery module 718 coordinates the delivery of feedback based on the analysis performed by the host 712. In response to the analysis module 716, delivery module 718 can manage the devices 702, 704, and 706, perform diagnostic data recovery, program the devices, and otherwise deliver information as needed. In some embodiments, the delivery module 718 can manage a web interface that can be accessed by patients or caregivers. The information gathered by an implanted device can be periodically transmitted to a web site that is securely accessible to the caregiver and/or patient in a timely manner. In other embodiments, a patient accesses detailed health information with diagnostic recommendations based upon analysis algorithms derived from leading health care institutions.

For example, the caregiver and/or patient can access the data and analysis performed on the data by accessing one or more general content providers. In one example, the patient's health information is accessed through a general portal such as My Yahoo provided by Yahoo! Inc. of Sunnyvale, Calif. A patient can access his or her My Yahoo homepage and receive information regarding current health and trends derived from the information gathered from the devices 702, 704, and 706, as well as other health information gathered from other sources. The patient may also access other information in addition to health information on the My Yahoo website, such as weather and stock market information. Other electronic delivery methods such as email, facsimile, etc. can also be used for alert distribution.

In an alternative embodiment, the data collected and integrated by the advanced patient system 700, as well as any analysis performed by the system 700, is delivered by delivery module 718 to a caregiver's hospital computer system for access by the caregiver. A standard or custom interface facilitates communication between the advanced patient management system 700 and a legacy hospital system used by the caregiver so that the caregiver can access all relevant information using a system familiar to the caregiver.

The advanced patient management system 700 can also be configured so that various components of the system (e.g., ITU 708, communication system 710, and/or host 712) provide reporting to various individuals (e.g., patient and/or caregiver). For example, different levels of reporting can be provided by (1) the ITU 708 and (2) the host 712. The ITU 708 may be configured to conduct rudimentary analysis of data gathered from devices 702, 704, and 706, and provide reporting should an acute situation be identified. For example, if the ITU 708 detects that a significant heart arrhythmia is imminent or currently taking place, the ITU 708 provides reporting to the patient in the form of an audible or visual alarm.

The host 712 can provide a more sophisticated reporting system. For example, the host 712 can provide exception-based reporting and alerts that categorize different reporting events based on importance. Some reporting events do not require caregiver intervention and therefore can be reported automatically. In other escalating situations, caregiver and/or emergency response personnel need to become involved. For example, based on the data collected by the advanced patient management system 700, the delivery module 718 can communicate directly with the devices 702, 704, and 706, contact a pharmacy to order a specific medication for the patient, and/or contact 911 emergency response. In an alternative embodiment, the delivery module 718 and/or the patient may also establish a voice communication link between the patient and a caregiver, if warranted.

In addition to forms of reporting including visual and/or audible information, the advanced patient management system 700 can also communicate with and reconfigure one or more of the devices 702, 704, and 706. For example, if device 702 is part of a cardiac rhythm management system, the host 712 can communicate with the device 702 and reconfigure the therapy provided by the cardiac rhythm management system based on the data collected from one or more of the devices 702, 704, and 706. In another embodiment, the delivery module 718 can provide to the ITU 708 recorded data, an ideal range for the data, a conclusion based on the recorded data, and a recommended course of action. This information can be displayed on the ITU 708 for the patient to review or made available on the peripheral device 709 for the patient and/or clinician to review.

One or more headings have been provided above to assist in describing the various embodiments disclosed herein. The use of headings, and the resulting division of the description by the headings, should not be construed as limiting in any way. The subject matter described under one heading can be combined with subject matter described under one or more of the other headings without limitation and as desired.

The systems and methods of the present disclosure can be implemented using a system as shown in the various figures disclosed herein including various devices and/or programmers, including implantable or external devices. Accordingly, the methods of the present disclosure can be implemented: (1) as a sequence of computer implemented steps running on the system; and (2) as interconnected modules within the system. The implementation is a matter of choice dependent on the performance requirements of the system implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

Embodiments of the invention may be implemented in one or a combination of hardware, firmware, and software. Embodiments of the invention may also be implemented as instructions stored on a machine-readable medium, which may be read and executed by at least one processor to perform the operations described herein. A machine-readable medium may include any mechanism for storing or transmitting information in a form readable by a machine (e.g., a computer). For example, a machine-readable medium may include read-only memory (ROM), random-access memory (RAM), magnetic disc storage media, optical storage media, flash-memory devices, electrical, optical, acoustical or other form of propagated signals (e.g., carrier waves, infrared signals, digital signals, etc.), and others.

In the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate preferred embodiment.

The claimed invention is:

1. A system for early detection of decompensation of heart failure, the system comprising:
   a first interface configured to receive urinalysis data that indicates whether decompensation of heart failure is present or impending, and to send the urinalysis data to a computer via a network;
   a second interface configured to receive data from a cardiac rhythm management device, the data from the cardiac rhythm management device capable of indicating whether decompensation of heart failure is present or impending, and to send the data from the device to the computer;
   a set of instructions stored in the computer, which when executed causes the computer to access the urinalysis data and the data from the cardiac rhythm management device, and based at least in part upon both the accessed urinalysis data and the data from cardiac rhythm management device, to detect and indicate decompensation of heart failure.

2. The system of claim 1, further comprising:
   a third interface configured to receive weight data, and to send the weight data to the computer.

3. The system of claim 2, wherein the set of instructions, when executed, further causes the computer to access the weight data, and to detect an impending decompensation of heart failure based at least in part upon the accessed data.

4. The system of claim 3, further comprising:
   a fourth interface configured to receive blood constituent concentration data, and to send the blood constituent concentration data to the computer.

5. The system of claim 4, wherein the set of instructions, when executed, further causes the computer to access the blood constituent concentration data, and to detect an impending decompensation of heart failure based at least in part upon the accessed data.

6. The system of claim 1, further comprising:
   a collection volume configured to hold a urine sample;
   a transmitter configured to propagate a signal through the urine sample; and
   a detector configured to receive the propagated signal, and to send a second signal standing in known relation to the received propagated signal to a processor in data communication with a memory storing a set of instructions, which when executed causes the processor to construct urinalysis data based upon the second signal, and to send the urinalysis data to the first interface.

7. The system of claim 6, wherein the urinalysis data comprises conductivity, specific gravity, color, or refractive index of the urine sample.

8. The system. of claim 6, wherein the propagated signal is an electromagnetic signal.

9. The system of claim 6, wherein the propagated signal is an acoustic signal.

10. The system of claim 1, further comprising:
    a collection volume configured to hold a urine sample;
    a strip having at least one chemically treated portion, the at least one portion being configured to contact the urine sample, and to change state in proportion to a concentration level of a constituent within the urine sample; and
    a detector configured to observe the state of the at least one portion, and to send a signal standing in known relation to the observed state to a processor in data communication with a memory storing a set of instructions, which when executed causes the processor to construct urinalysis data based upon the signal, and to send the urinalysis data to the first interface.

11. The system of claim 10, wherein the state comprises color of the at least one chemically treated portion.

12. The system of claim 10, wherein the urinalysis data comprises information regarding a concentration level of a given constituent in the urine sample.

13. A method of early detection of decompensation of heart failure in a patient, comprising:
    comparing a urinalysis measurement with a first boundary to determine if the urinalysis measurement is abnormal for the patient, wherein the urinalysis measurement provides data that indicates whether decompensation of heart failure is present or impending;
    comparing a measurement made by a cardiac rhythm management device with a second boundary to determine if the device measurement is abnormal for the patient wherein the urinalysis measurement provides data capable of indicating whether decompensation of heart failure is present or impending; and
    determining and indicating whether decompensation of heart failure is imminent for the patient on the basis of at least both of the comparisons.

14. The method of claim 13, wherein the urinalysis measurement comprises conductivity, specific gravity, color, or refractive index of a urine sample.

15. The method of claim 13, wherein the urinalysis measurement comprises information regarding a concentration level of a given constituent in the urine sample.

16. The method of claim 15, wherein the constituent is protein, albumin, microalbumin, uric acid, urea, creatinine, sodium, leukocyte estrase, nitrites, bilirubin, ketones, glucose, or heart failure medication.

17. The method of claim 16, wherein the urinalysis measurement comprises a ratio of urine sodium to urine creatinine.

18. The method of claim 15, further comprising:
measuring a blood concentration level of the given constituent;
measuring a urine production rate; and
determining a clearance rate of the given constituent on the basis of the measurements.

19. The method of claim 13, further comprising:
comparing a weight measurement with a third boundary to determine if the weight is abnormal for the patient; and
determining whether decompensation of heart failure is imminent for the patient on the further basis of the weight comparison.

20. The method of claim 13, wherein the measurement made by a cardiac rhythm management device is a transthoracic impedance measurement.

21. A computerized method of early detection of decompensation of heart failure in a patient, comprising:
accessing a set of urinalysis data, each datum within the data set describing a particular characteristic of the patient's urine at differing points in time, wherein the urinalysis data indicates whether decompensation of heart failure is present or impending;
determining a boundary from the accessed urinalysis data set;
comparing a data point describing the particular characteristic of the patient's urine with the boundary; and
detecting and indicating impending decompensation of heart failure for the patient, based at least in part upon the comparison.

22. The method of claim 21, the act of determining the boundary comprises:
determining the mean of the urinalysis data set; and
adding a quantity to the mean to arrive at the boundary.

23. The method of claim 22, wherein the quantity is a value standing in known relation to the standard deviation of the urinalysis data set.

24. The method of claim 21, wherein the act of determining the boundary comprises:
finding a first value greater than a given percentage of the data within the urinalysis data set; and
setting the boundary to a second quantity standing in known relation to the first quantity.

25. A computerized method of early detection of decompensation of heart failure in a patient, comprising:
accessing a plurality of sets of urinalysis data, wherein the urinalysis data indicates whether decompensation of heart failure is present or impending, and wherein for a given one of the urinalysis data sets, each datum therein describes a particular characteristic of the patient's urine at a differing points in time, and wherein each of the urinalysis data sets corresponds to a different characteristic of the patient's urine;
determining a plurality of boundaries, each of the boundaries corresponding to a given one of the plurality of urinalysis data sets;
comparing each of a plurality of data points describing characteristics of the patient's urine with a corresponding one of the plurality of boundaries; and
detecting and indicating impending decompensation of heart failure for the patient, based at least in part upon the comparisons.

26. The method of claim 25, wherein the act of detecting and indicating impending decompensation of heart failure comprises:
detecting and indicating impending decompensation of heart failure upon the occurrence of any of the data points falling outside of their respective boundaries.

27. The method of claim 25, wherein the act of detecting and indicating impending decompensation of heart failure comprises:
counting the number of data points falling outside of their respective boundaries; and
detecting and indicating impending decompensation of heart failure if the counted number exceeds a threshold.

28. The method of claim 25, wherein the act of detecting and indicating impending decompensation of heart failure comprises:
assigning a weight to each of the boundaries;
tallying a weighted count of the number of data points falling outside of their respective boundaries; and
detecting and indicating impending decompensation of heart failure if the weighted count exceeds a threshold.

29. The method of claim 25, wherein the act of detecting and indicating impending decompensation of heart failure comprises:
identifying a subset of boundaries;
detecting and indicating impending decompensation of heart failure if one of the data points corresponding to one of the subset of boundaries falls outside of its respective boundary.

30. The method of claim 25, wherein the data points are obtained by a device at a location remote from a computer executing the computerized method.

31. The method of claim 30, wherein the remote location comprises the patient's home.

32. A system for early detection of decompensation of heart failure, the system comprising:
a means for obtaining urinalysis data that indicates whether decompensation of heart failure is present or impending; and
a means for detecting and indicating impending decompensation of heart failure, based upon the urinalysis data.

\* \* \* \* \*

UNITED STATES PATENT AND TRADEMARK OFFICE
CERTIFICATE OF CORRECTION

PATENT NO.       : 7,606,617 B2                                           Page 1 of 1
APPLICATION NO.  : 11/343441
DATED            : October 20, 2009
INVENTOR(S)      : Ramesh Wariar It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 881 days.

Signed and Sealed this

Twelfth Day of October, 2010

David J. Kappos
*Director of the United States Patent and Trademark Office*